US008461302B2

(12) United States Patent
Jewell et al.

(10) Patent No.: US 8,461,302 B2
(45) Date of Patent: Jun. 11, 2013

(54) PURIFICATION OF RECOMBINANT HUMAN FACTOR XIII (75) Inventors: Carol Jewell, Redmond, WA (US); Hardarshan Cheema, Durham (GB); Deborah Hogg, Warrington (GB); Wenmao Meng, Newcastle upon Tyne (GB); Ray O'Donnell, North Stainley North Yorkshire (GB); Ewan Robertson, Fairfield Stockton-on-Tees (GB); Andrew Topping, Milford, MA (US)

(73) Assignee: Zymogenetics, Inc., Seattle, WA (US)

( * ) Notice: Subject to any disclaimer, the term of this patent is extended or adjusted under 35 U.S.C. 154(b) by 805 days.

(21) Appl. No.: 11/720,032

(22) PCT Filed: Nov. 23, 2005

(86) PCT No.: PCT/EP2005/056169
§ 371 (c)(1),
(2), (4) Date: Mar. 21, 2008

(87) PCT Pub. No.: WO2006/056575
PCT Pub. Date: Jun. 1, 2006

(65) Prior Publication Data
US 2008/0281080 A1 Nov. 13, 2008

Related U.S. Application Data (60) Provisional application No. 60/630,614, filed on Nov. 23, 2004.

(51) Int. Cl.
*A61K 35/14* (2006.01)
*A61K 38/36* (2006.01)
*C07K 14/745* (2006.01)
*C07K 1/18* (2006.01)
*C07K 1/22* (2006.01)

(52) U.S. Cl.
USPC ........... 530/382; 530/412; 530/413; 530/415; 530/416; 530/417

(58) Field of Classification Search
None
See application file for complete search history.

(56) References Cited

U.S. PATENT DOCUMENTS

| 4,265,233 | A | 5/1981 | Sugitachi et al. |
| 4,298,598 | A | 11/1981 | Schwarz et al. |
| 4,362,567 | A | 12/1982 | Schwarz et al. |
| 4,377,572 | A | 3/1983 | Schwarz et al. |
| 4,414,976 | A | 11/1983 | Schwarz et al. |
| 4,453,939 | A | 6/1984 | Zimmerman et al. |
| 4,597,899 | A | 7/1986 | Falke |
| 5,114,916 | A | 5/1992 | Shirahata et al. |
| 5,204,447 | A | 4/1993 | Bishop et al. |
| 5,607,917 | A | 3/1997 | Carter et al. |
| 5,612,456 | A | 3/1997 | Bishop et al. |
| 7,008,926 | B2 | 3/2006 | Bishop |

| 2004/0014657 | A1 | 1/2004 | Ohrstrom et al. |
| 2007/0015709 | A1 | 1/2007 | Ohrstrom et al. |
| 2007/0021340 | A1 | 1/2007 | Ohrstrom et al. |
| 2011/0218138 | A1 | 9/2011 | Perez et al. |

FOREIGN PATENT DOCUMENTS

| EP | 0268772 | 6/1988 |
| GB | 2102811 A | 2/1983 |
| JP | 2-247199 | 10/1990 |
| JP | 7-506479 | 7/1995 |
| JP | 2004-123566 | 4/2004 |
| JP | 08505129 | 2/2008 |
| WO | 90/05777 A1 | 5/1990 |
| WO | WO 93/03147 | 2/1993 |
| WO | WO 01/85199 | 11/2001 |
| WO | 02/36155 A1 | 5/2002 |
| WO | 02/38167 A2 | 5/2002 |
| WO | WO 2004/007533 A1 | 1/2004 |

OTHER PUBLICATIONS

Ando, Y., et al. 1987 J Biochem 101: 1331-1337.*
Greenberg, C.S. et al., "The Zymogen Forms of Blood Coagulation Factor XIII Bind Specifically to Fibrinogen", The Journal of Biological Chemistry, 1982, vol. 257, No. 11, pp. 6096-6101.
Ichinose, A. et al., "Amino Acid Sequence of the a Subunit of Human Factor XIII", Biochemistry, 1986, vol. 25, pp. 6900-6906.
Ichinose, A. et al., "Amino Acid Sequence of the b Subunit of Human Factor XIII, a Protein Composed of Ten Repetitive Segments", Biochemistry, 1986, vol. 25, pp. 4633-4638.
Guillevin, L. et al., "Treatment of Progressive Systemic Sclerosis using Factor XIII", Pharmatherapeutica, 1985, vol. 4, No. 2, pp. 76-80.
Grivaux, M. et al., Carcinome bronchiolo-alveolaire compliquant une sclerodermie generalisee traitee au long cours par le facteur XIII, Rev. Pneumol. Clin., 1987, vol. 43, pp. 102-103.
Suzuki R. et al., Thrombosis and Haemostasis, 1987, vol. 58, No. 509.
Henze, T.A. et al., Thrombosis and Haemostasis, 1987, vol. 58, No. 513.
Kuratsuji, T. et al., "Factor XIII Deficiency in Antibiotic-Associated Pseudomembranous Colitis and Its Treatment with Factor XIII Concentrate", Haemostasis, 1982, vol. 11, pp. 229-234.

(Continued)

*Primary Examiner* — Marsha Tsay
(74) *Attorney, Agent, or Firm* — Michael J. Brignatti (57) ABSTRACT

The present invention provides improved methods for the purification of factor XIII. In particular, the methods provide compositions containing 5% or less contaminating proteins. In particular embodiments of the present invention the methods provide purified factor XIII compositions comprising less than 1% activated factor XIII, less than 2% protein aggregates, and/or less than 5% charge isomers of factor XIII. The methods do not require the use a precipitation or crystallization step common to prior methods of isolating factor XIII. Instead, the method uses immobilized metal affinity chromatography to remove various contaminants common to recombinant expression of factor XIII. Further, a combination of various chromatography methods including ion exchange chromatography, hydrophobic affinity chromatography, and immobilized metal affinity chromatography comprise a simple and less expensive method to produce a pharmaceutical grade factor XIII product at high yield.

11 Claims, 8 Drawing Sheets

OTHER PUBLICATIONS

Delbarre, F. et al., "Factor XIII Treatment for Scleroderma", Lancet, 1981, vol. 318, No. 8329, p. 204.

Vogt, R.N. et al., "The Metabolism of Nitrosothiols in the Mycobacteria: Identification and Characterization of S-Nitrosomycothiol Reductase", Biochem. J., 2003, vol. 374, pp. 657-666.

De Backer-Royer, C. et al., "Purification and Properties of Factor XIII From Human Placenta", Int. J. Biochem., 1992, vol. 24, No. 1, pp. 91-97.

Aräns, R.A.S et al. Blood Role of Factor XIII in Fibrin Clot Formation and.. 2002 100 3 743-754.

Ando et al., The Journal of Biochemistry, High-Performance Liquid Chromatographic Assay of Transglutaminase and Its Application to the Purification of Human Erythrocyte Transglutaminase and Platelet Factor XIII, 1987, vol. 101, Issue 6, pp. 1331-1337.

Bergamini, C.M et al. Biochemistry International. Purification of Testicular Transglutaminase by . . . 1992 27 4 557-565.

Bishop, P.D. et al. Biochemistry Expression, Purification, and Characterization of . . . 1990 29 7 1861-1869.

Lai, T-S et al. Protein Expression and Purification Purification and Characterization of . . . 1994 5 2 125-132.

Wilhelm, B et al. Journal of Chromatography Transglutaminases: Purification and Activity Assays 1996 684-163-177.

\* cited by examiner

PURIFICATION OF RECOMBINANT HUMAN FACTOR XIII

CROSS-REFERENCE TO RELATED APPLICATIONS

This application is a 35 U.S.C. §371 national stage application of International Patent Application PCT/EP2005/056169 (published as WO 2006/056575), filed Nov. 23, 2005, which claimed priority of U.S. patent application Ser. No. 60/630,614, filed Nov. 23, 2004.

BACKGROUND OF THE INVENTION

Factor XIII, also known as fibrin stabilizing factor, fibrinoligase, or plasma transglutaminase, is a plasma glycoprotein that circulates in blood as a zymogen ($M_r$ of about 320 kDa) complexed with fibrinogen. (Greenberg and Shuman, *J. Biol. Chem.* 257:6096-6101 (1982)). Plasma factor XIII zymogen is a tetramer consisting of two a subunits and two b subunits. Each subunit has a molecular weight of about 83,000 Da, and the complete protein has a molecular weight of approximately 320 kDa. The a subunit contains the catalytic site of the enzyme, while the b subunit is thought to stabilize the a subunit or to regulate the activation of factor XIII. The amino acid sequences of the a and b subunits are known. (Ichinose et al., *Biochemistry* 25:6900-6906 (1986); Ichinose et al., *Biochemistry* 25:4633-4638 (1986)). Recombinant expression of biologically active factor XIII has been described, see for example, EP 0 268 772 B1.

In vivo, activated factor XIII catalyzes cross-linking reactions between other protein molecules. During the final stages of blood coagulation, thrombin converts factor XIII zymogen to an intermediate form, which then dissociates in the presence of calcium ions to produce activated factor XIII. Placental factor XIII is activated upon cleavage by thrombin. Activated factor XIII is a transglutaminase that catalyzes the cross-linking of fibrin polymers through the formation of intermolecular $\xi(\delta)$-glutamyl lysine bonds, thereby increasing clot strength. This cross-linking reaction requires the presence of calcium ions. Activated factor XIII also catalyzes the cross-linking of the δ-chain of fibrin to $\alpha_2$-plasmin inhibitor and fibronectin, as well as the cross-linking of collagen and fibronectin, which may be related to wound healing. The covalent incorporation of $\alpha_2$-plasmin inhibitor into the fibrin network can increase the resistance of the clot to lysis.

Factor XIII deficiency results in "delayed bleeding," but does not affect primary hemostasis. Current treatment practices for patients having factor XIII deficiencies generally involve re-placement therapy with purified factor XIII isolated from natural sources.

Factor XIII is also useful in the treatment of patients with scleroderma (Delbarre et al., *Lancet* 2:204 (1984); Guillevin et al., *Pharmatherapeutica* 4:76-80 (1985); Grivaux and Pieron, *Rev. Pnemnol. Clin.* 43:102-103 (1987)), ulcerative colitis (Suzuki and Takamura, *Throm. Haemostas.* 58:509 (1987); U.S. Pat. No. 5,378,687), colitis pseudomembranous (Kuratsuji et al., *Haemostasis* 11:229-234 (1982) and as a prophylactic of rebleeding in patients with subarachnoid hemorrhage (Henze et al., *Thromb. Haemostas.* 58:513 (1987), in addition to other conditions. Furthermore, factor XIII has been demonstrated to be useful as a component of tissue adhesives (U.S. Pat. Nos. 4,414,976; 4,453,939; 4,377,572; 4,362,567; 4,298,598; 4,265,233 and U.K. Patent No. 2 102 811 B). Another use of factor XIII includes reducing blood loss in patients undergoing surgery (U.S. Pat. No. 5,607,917).

Methods for the recombinant production of human factor XIII are known in the art. See for example, European Patent No. 0 268 772 B1. Also, methods for the purification of factor XIII from biological sources using crystallization and/or precipitation steps combined with certain chromatography methods are known (U.S. Pat. Nos. 4,597,899; 5,204,447 and 5,612,456). Although each of the prior methods results in the enrichment of factor XIII, each of the methods is either complex and/or expensive for the isolation of factor XIII at high yield. What is needed in the art is a simpler, less expensive method for the isolation of highly purified factor XIII, i.e., compositions that are greater than 95% pure with respect to contaminating proteins would be particularly desired. Methods that can provide compositions comprising factor XIII that is 1% or less activated factor XIII, contain less than 2% protein aggregates, and/or less than 5% charge isomers of factor XIII, while providing a high yield would also be particularly desired.

BRIEF SUMMARY OF THE INVENTION

The present invention provides methods for the isolation of highly purified factor XIII. In a particular embodiment, using the methods disclosed, a factor XIII composition that is at least 95% pure with respect to contaminating proteins can be obtained. These methods are particularly adapted for the purification of recombinant factor XIII from a recombinant host cell. In a particular embodiment the recombinant host cell is a recombinant yeast cell and the methods provide for the purification of yeast-produced recombinant human factor XIII.

The present invention provides purification methods that do not require a precipitation and/or a crystallization step. The present methods also do not require the use of expensive antibodies or monoclonal antibodies specific for factor XIII for purification of the factor. Within one typical embodiment a biological fluid comprising recoverable amounts of factor XIII is fractionated by immobilized metal affinity chromatography to produce a highly concentrated factor XIII product that does not contain proteins of the biological fluid that have been found in factor XIII product purified by other typical purification methods. In a particular embodiment, the biological fluid is a lysate from a recombinant yeast cell transformed to produce factor XIII wherein the methods of the present invention remove yeast proteins that typically remain with prior purification methods.

In a particular embodiment of the present invention immobilized metal affinity chromatography is combined with other affinity purification techniques. Typically, immobilized metal affinity chromatography is combined in any order with anion exchange and hydrophobic interaction fractionation to purify the factor XIII. Specifically in this embodiment a biological fluid comprising recoverable amounts of factor XIII is first partially purified by anion exchange fractionation prior to using a combination of immobilized metal affinity chromatography, hydrophobic interaction fractionation and anion exchange chromatography to complete the purification process. In a particular embodiment the biological fluid is first partially purified by anion exchange fractionation to produce a first fraction enriched for factor XIII; this first fraction is further fractionated by hydrophobic interaction fractionation to produce a second fraction enriched for factor XIII; subsequently the second enriched fraction is further fractionated by immobilized metal affinity chromatography to produce a third fraction enriched for factor XIII. This third fraction can optionally be further fractionated by anion exchange fractionation to produce a highly purified factor XIII-containing peak fraction.

The biological fluid comprising recoverable amounts of factor XIII can include cell culture supernatants, cell lysates, clarified cell lysates, cell extracts, tissue extracts, blood, plasma, and fractions thereof. In a typical embodiment of the present invention the biological fluid is a cell lysate, particularly a cell lysate of a recombinant cell that has been engineered to produce factor XIII.

Factor XIII of the present invention comprises any factor XIII including but not limited to a mammalian factor XIII, including in particular human factor XIII. Factor XIII can include polyprotein comprising the $a_2$ dimer, comprising the $a_2b_2$ tetramer, and the like. Typically, the factor XIII is the $a_2$ subunit dimer produced by a recombinant cell. The recombinant cell of the present invention can include bacterial, yeast and cultured mammalian cells. Typically, the yeast cells used for recombinant expression of factor XIII include those of the genus *Saccharomyces*, including for example, *Saccharomyces cerevisiae*, and species of *Pichia* and *Kluyveromyces*.

In one particular embodiment of the present invention the anion exchange fractionation of the biological sample comprising factor XIII is carried out on a substrate, solid phase, or media that has been derivatized with DEAE. Prior to elution of the sample from the anion exchange medium the sample can be washed with a buffer solution comprising a density modifier, such as a sugar, e.g., sucrose, or glycerol to remove cellular debris. Hydrophobic interaction fractionation as used in the present invention comprises use of a chromatography media that has been derivatized with a butyl, phenyl or octyl group. In a particularly preferred embodiment the hydrophobic interaction chromatography media is derivatized with a phenyl group. Use of the chromatography media derivatized with a phenyl group has been found to require a lower salt buffer to elute the fractions comprising the largest amounts of factor XIII.

Immobilized metal affinity chromatography as used in the processes of the present invention comprises the use of chromatographic media that is charged with, for example $Cu^{2+}$, $Zn^{2+}$, or $Ni^{2+}$. In a particular embodiment the chromatographic media charged with $Ni^{2+}$ has been found to give the highest yield of factor XIII. Further, the factor XIII enriched fraction collected at each step of the disclosed process can be filtered to remove any particulates or aggregates that may have formed during each step in the process.

One particularly preferred embodiment of the present invention comprises fractionating the biological fluid by anion exchange with an anion exchange media, e.g., a DEAE derivatized chromatography media, to produce a first fraction enriched for factor XIII; this first fraction is further fractionated by hydrophobic interaction employing a phenyl derivatized chromatography media to produce a second fraction enriched for factor XIII; subsequently the second enriched fraction is further purified by immobilized metal affinity chromatography comprising a $Ni^{2+}$ charged chromatography media to produce a third fraction enriched for factor XIII; the third fraction is finally fractionated by anion exchange with a QAE derivatized chromatography media to produce a purified factor XIII-containing peak fraction. In a typical embodiment the factor XIII product produced by this process is at least 95% pure with respect to contaminating proteins. In particular embodiments, the product can comprise less than 5% yeast proteins. Further the product can comprise less than 1% activated factor XIII, less than 2% aggregates and/or can also comprise less than 5% charge isomers of factor XIII. Yield for the process can be at least about 45%.

A further understanding of the nature and advantages of the invention will become apparent by reference to the remaining portions of the specification.

BRIEF DESCRIPTION OF THE DRAWINGS

FIGS. 1A through 1C depict flow charts for two purification processes for recombinant human factor XIII. The first process comprises anion exchange fractionation followed by a hydrophobic interaction separation using a butyl derivatized media and a second anion exchange separation. The second purification process adds an immobilized metal ion affinity chromatography (IMAC) step and changes the hydrophobic interaction chromatography (HIC) derivatized media to one containing a phenyl group.

FIG. 4 depicts the results from the SDS-PAGE analysis of fractions collected from the immobilized metal affinity chromatography elution. Lane 1: molecular weight standards; Lane 2: load; Lane 3: flow through; Lane 4: flow through salt wash; Lane 5: blank; Lane 6: eluate pool; Lane 7: blank; Lane 8: eluate pool at 1:2 dilution; Lane 9: bovine serum albumin standard; Lane 10: recombinant human factor XIII standard as isolated by the method of FIG. 1.

FIGS. 5A and 5B depict the results from the SDS-PAGE analysis of fractions collected from the anion exchange step following IMAC. Lane 1: molecular weight standards; Lane 2: Q-load; Lane 3: eluate fraction 1; Lane 4: eluate fraction 2; Lane 5: eluate fraction 3; Lane 6: eluate fraction 4; Lane 7: eluate fraction 5; Lane 8: eluate fraction 6; Lane 9: bovine serum albumin standard; Lane 10: recombinant human factor XIII standard; Lane 11: molecular weight standard; Lane 12: eluate fraction 7; Lane 13: eluate fraction 8; Lane 14: eluate fraction 9; Lane 15: eluate fraction 10; Lane 16: eluate fraction 11; Lane 17: post peak flow through; Lane 18: Q eluate pool diluted; Lane 19: bovine serum albumin standard; Lane 20: recombinant human factor XIII standard.

FIG. 6 depicts the results from the SDS-PAGE silver stain analysis of the final product. Lane 1: molecular weight standards; Lane 2: conditioned Q-pool (2.5%); Lane 3: permeate; Lane 4: concentrate (92.54 g/L); Lane 5: diafiltrate (10.6 g/L); Lane 6: diafiltrate diluted (5.3 g/L); Lane 7: final dilution (2.4 g/L); Lane 8: sterile filtered product (2.4 g/L); Lane 10: recombinant human factor XIII standard.

DETAILED DESCRIPTION OF THE INVENTION

The present invention provides methods for the isolation of highly purified factor XIII by use of fractionation with an immobilized metal affinity substrate. Using the methods disclosed, a highly purified factor XIII that is at least 95% pure with respect to contaminating proteins can be obtained more simply and less expensively than with prior methods. The methods of the present invention are particularly adapted for the purification of recombinant factor XIII from a biological fluid, including a biological fluid comprising a lysate of a recombinant yeast host cell that produces human factor XIII. In certain particular embodiments the methods can further provide a composition that contains less than 2% protein aggregates and/or less than 1% activated factor XIII. Further, in a particular embodiment of the invention the purified compositions produced by the methods of the present invention comprise less than 5% charge isomers of factor XIII. Unlike some earlier methods for the purification of factor XIII no precipitation and/or crystallization step is required. (U.S. Pat. No. 5,612,456)

The term "factor XIII" as used herein means a factor XIII polyprotein comprising the $a_2$ dimer, a factor XIII polyprotein comprising the $a_2b_2$ tetramer, or other combinations of a and b subunits as long as the polyprotein does not demonstrate substantial activated factor XIII activity.

According to the present invention, factor XIII is purified from a variety of biological fluids. A "biological fluid" as used herein is any fluid derived from or containing cells, cell components or cell products. Biological fluids include, but are not limited to, cell culture supernatants, cell lysates, clarified cell lysates, cell extracts, tissue extracts, blood, plasma, and fractions thereof. Cell lysates can be made from cells that naturally produce factor XIII in recoverable amounts, such as placental cells, and the like. However, typically lysates and extracts of cells are prepared from cells or cell lines that have been genetically modified to produce factor XIII. Biological fluids can also include culture medium into which factor XIII has been secreted by a cell that has been genetically modified to express and secrete factor XIII. In a particular embodiment of the present invention the biological fluid is a lysate or clarified lysate obtained from a yeast cell that has been transformed with a nucleic acid sequence to produce factor XIII, although the cell can be any genetically modified cell. The methods of the present invention can be used to produce preparations that contain significantly less than 200 to 300 ppm yeast protein.

Further, as with prior methods, the present methods also remove activated factor XIII. In a particular embodiment of the present methods a composition can be provided that contains not more than 1% activated factor XIII and typically less than 1%. In certain embodiments of the process charge isomers of factor XIII that might be present in a factor XIII fraction can also be removed.

With the present invention it has been found that an immobilized metal affinity chromatography (IMAC) substrate provides good binding properties for recombinant human factor XIII and results in the removal of contaminants found in some typical prior purification processes, including a purification process disclosed herein. IMAC substrates have been found to further provide the additional benefit of desalting the fractions enriched for recombinant factor XIII and also significantly reducing the loading volume for further downstream processing. Generally, IMAC exploits a molecule's affinity for chelated metal ions for separation. Many proteins form complexes with transition metal ions such as $Cu^{2+}$, $Zn^{2+}$, and $Ni^{2+}$. Elution of a protein from such a complex is typically accomplished by reducing the pH to below 6, more typically reducing the pH to about 2 or 3, or by keeping a constant pH and providing an increase in a competing ion, such as imidazole, histidine or ammonium chloride. In the present invention, factor XIII is apparently weakly adsorbed to the immobilized metal ion while the majority of contaminating proteins are tightly bound to the column resin. Factor XIII is eluted from the column by reducing the salt concentration of the elution buffer without the need for the addition of a chelator or decreasing the pH of the elution buffer. The enriched factor XIII fraction eluted from the IMAC separation step can be sufficiently concentrated that it may be necessary to dilute the factor XIII enriched fraction to prevent precipitation. Selection of the dilution buffer is dependent on the next step selected in the downstream process. In one particular embodiment of the present invention a Tris buffer at about pH 7.6 to about pH 8.0 is used for dilution.

In a typical embodiment of the present invention immobilized metal affinity fractionation is combined with other affinity purification methods. In a particular embodiment IMAC is combined with anion exchange chromatography and hydrophobic affinity chromatography while retaining the pH of the solution above about 7.0 allowing for the enrichment of factor XIII without the need for a precipitation and/or crystallization step. A second anion exchange step can also be added to the purification method. Although one particular embodiment of the invention provides the various affinity purification methods and steps in a particular order, no particular order of steps is required to provide a purified factor XIII composition of the present invention. An artisan of ordinary skill in the art with the guidance provided in the present disclosure can alter the order of one or more fractionation methods to achieve a similar result.

As noted above, recombinant cells and cell lines are typical sources of factor XIII. Human and mammalian factor XIII cDNA clones and production of factor XIII in recombinant cells, including bacteria, yeast and cultured mammalian cells has been described. (Grundmann et al., Published Australian patent application 69896/87; European Patent No. EP 268 772 B1, and International Patent Publication No. WO 91/14780). Typically, the host cells used for producing factor XIII include yeast, such as baker's yeast (*Saccharomyces cerevisiae*) and species of *Pichia* and *Kluyveromyces*. Methods for expressing cloned DNA sequences are well known in the art. Briefly, a DNA sequence encoding factor XIII is operably linked to a suitable promoter and terminator sequence in a vector compatible with the chosen host cell or cell line. The vector is then inserted into the host cell and the resulting recombinant cells are cultured to produce factor XIII. Depending on the particular host cell and the expression cassette utilized, the factor XIII can be either secreted from the cell or retained in the cytoplasm.

When using cells that do not secrete factor XIII, the cells can be centrifuged and the cell fraction recovered. Typically, centrifugation is at a moderate speed (e.g., about 10,000×g) or filtration (e.g., microfiltration (MF)) can be used. In one method disclosed herein microfiltration is used to separate the host cells from the culture medium and to wash the cells prior to lysis. The cell culture can also be conditioned without collection of the cell fraction by adjusting the pH to about 8.5 with a buffer (e.g., Tris, and the like) and a divalent chelating agent (e.g., EDTA, and the like) and treated to produce a conditioned cell culture. In a specific embodiment of the present invention collection of the cell fraction is not required and the conditioned cell culture is processed directly to lyse the cells. In either process the cells are lysed or broken to release the cell contents including the recombinant factor XIII to form a crude lysate. Lysis can be accomplished by a number of means well known to the skilled artisan including homogenization, sonication, or solubilization of the cell membrane, and the like.

When working with crude cell lysates, which are likely to contain high levels of proteases, it is preferred to minimize the time in which the lysate is in a concentrated form. This can be readily achieved by quickly diluting the lysate, typically in a cool (about 2° C. to about 5° C.) diluent, such as water or an appropriate buffer. Dilution can also be required to reduce the conductivity of the lysate to below that required for downstream processing. In general, the lysate will be diluted about 1 to 5 fold relative to the starting cell slurry, but the actual amount of dilution will be determined by the characteristics of the cell lysate and the chromatography medium selected for the next step in the downstream process. In a specific embodiment of the present invention the conductivity is reduced to below 4.4 mS/cm to ensure capture by an anion exchange medium which can be used in a subsequent step in the purification process.

In one method of the present invention where IMAC is combined with other affinity purification methods, the diluted cell lysate is first fractionated by anion exchange, to produce a first fraction enriched for factor XIII. Typically, the diluted cell lysate is passed over a column comprising anion exchange medium at a pH of about 7.2 to about 8.2, and more typically at a pH of greater than about 7.5. Subsequent to a wash step, the factor XIII is fractionated or eluted from the anion exchange medium using a suitable elution buffer. Suitable anion exchange media for this step include PEI, DEAE, QAE and Q derivatives of, for example, dextran, agarose, cellulose, polyacrylamide, specialty silicas, and the like. DEAE STREAM-LINE resin (Pharmacia, Piscataway, N.J.) in an expanded bed chromatography column is particularly preferred for processes where it is necessary to remove cellular debris and other material from the culture and lysis of recombinant cells. A density modifier comprising a sugar, such as sucrose, or glycerol (i.e., at a concentration of about 1 to about 5%) can be included in the wash step to assist in the clearance of solids and cell debris from the column prior to elution. Further, before fractionation the density modifier can be washed from the column with a buffer solution. Fractionation of the factor XIII to form a first factor XIII enriched fraction can use a gradual salt gradient, but typically a step process is used to reduce the volume of the fraction enriched for factor XIII in the subsequent process steps. In a preferred embodiment a step gradient of an elution buffer comprising 20 mM Tris/80 mM $Na_2SO_4$, pH 7.8, is used.

The first factor XIII enriched fraction is further enriched by hydrophobic interaction chromatography to form a second factor XIII enriched fraction. Suitable chromatographic media include a solid phase derivatized with phenyl, butyl, or octyl groups and acrylic resins. In a particularly preferred embodiment of the present invention it was discovered that the phenyl derivatized media allowed for elution of the factor XIII enriched fraction using a lower salt buffer. It was also found that additional yeast proteins were removed using the phenyl derivatized chromatography media as compared to a purification process using a butyl derivatized media. The adsorbed factor XIII can be eluted from the column by use of a descending salt gradient or a step wash. Peaks enriched for factor XIII are pooled, sampled for analysis of factor XIII activity or protein concentration and form a second fraction enriched for factor XIII.

Figure 1A:
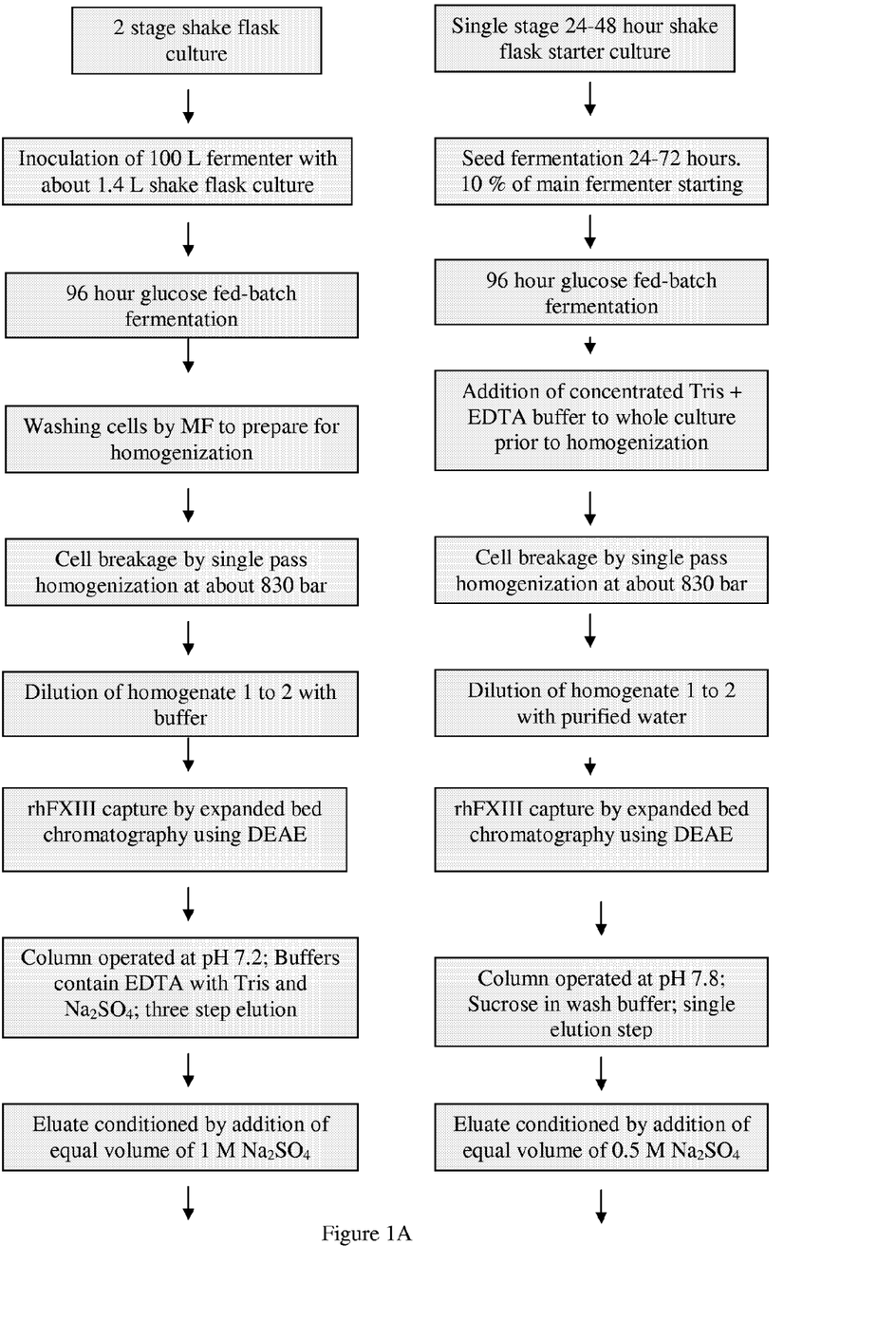
Figure 1B:
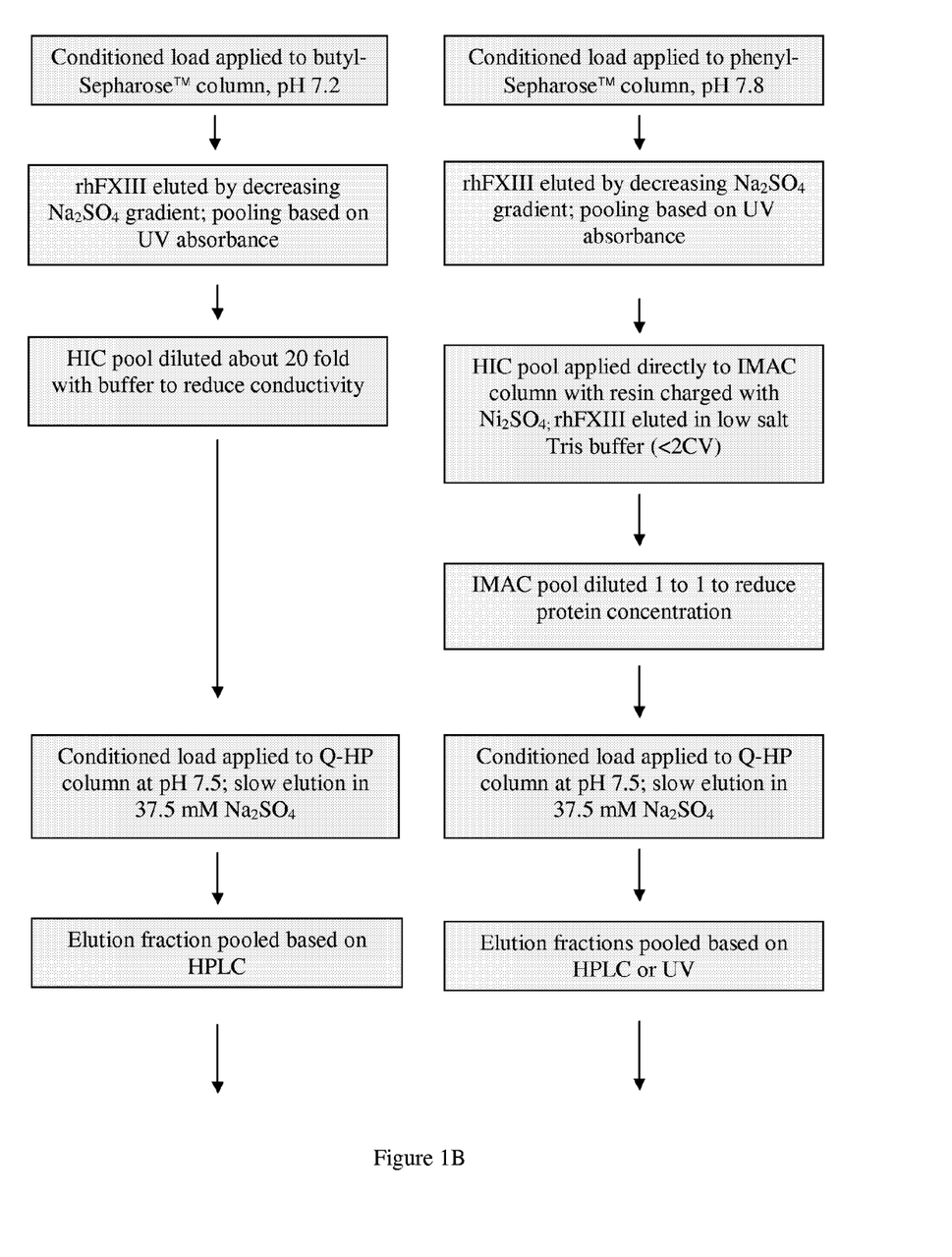
Figure 1C:
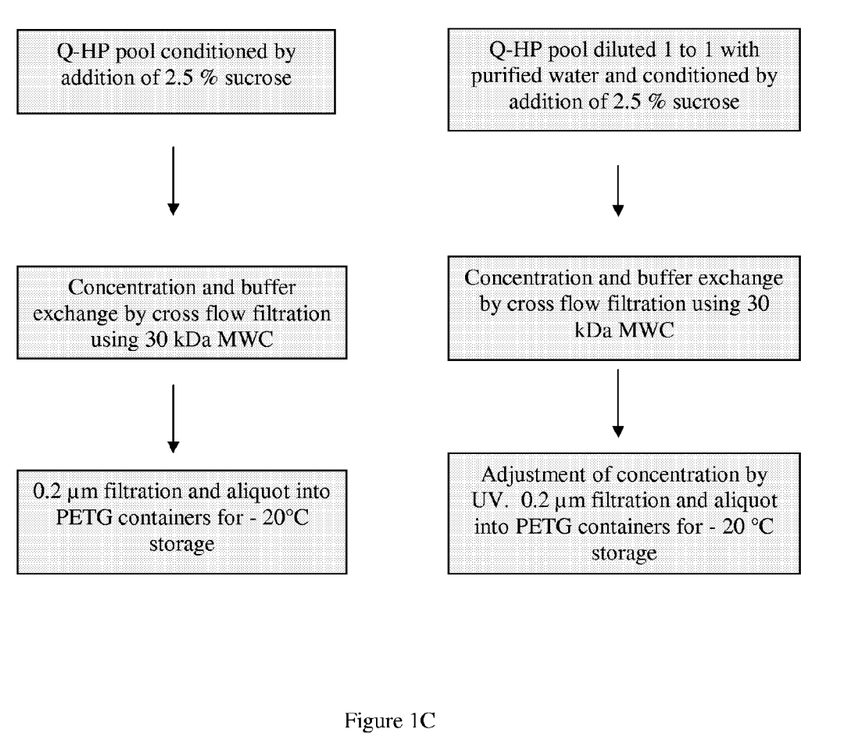

The second fraction enriched for factor XIII is further purified by immobilized metal affinity chromatography (IMAC) as described above. It has been found that the addition of IMAC in the purification process for factor XIII provides for the removal of lower molecular weight contaminants that have been observed in other processes for the purification of factor XIII. For example, the process of the present invention comprising IMAC demonstrates improved purification of factor XIII when compared to the process depicted in the left column of FIG. 1A-1C. Further, IMAC was found to produce a very concentrated factor XIII enriched fraction which resulted in a reduced load volume for further downstream processing. For a 100 L fermentation as demonstrated herein the reduction in load volume is typically on the order of about 30-fold.

In a particular embodiment of the present invention, a final anion exchange chromatography step can be included to remove any activated factor XIII and/or to separate any charge isomers of factor XIII that may be present in the third enriched factor XIII fraction. The final purified factor XIII enriched fraction can be eluted from the anion exchange column using an increasing salt gradient or a step elution. The peak fractions are pooled, diluted with an equal amount of purified water and can be conditioned by the addition of, for example, 2.5% (w/v) sucrose. The pooled fractions are then concentrated and the buffer can be exchanged to produce a final formula product.

Within the above-described methods the fractions enriched for factor XIII can be filtered prior to each of the various fractionation steps. Filtration can be carried out using a filter having a pore size of, for example, about 0.2 μm.

Purity of the factor XIII compositions prepared according to the present invention can be monitored by conventional means. Following individual separation steps, peak fractions can be identified by absorbance at 280 nm. Purified factor XIII can be quantitated by amino acid analysis, activity assay, and the like. Each assay is well known to the skilled artisan. Activated factor XIII content can be measured by carrying out activity assays with and without thrombin treatment. Contamination of recombinant factor XIII preparation by host cell protein can be assayed by immunological methods, such as enzyme-linked immunoassay (ELISA), polyacrylamide gel electrophoresis, and the like. Such assays will be designed with levels of sensitivity suitable for use within the pharmaceutical art.

EXAMPLES

The following examples are provided merely as illustrative of various aspects of the invention and should not be construed to limit the invention in any way.

This example describes two processes used to purify recombinant human factor XIII (rhFXIII) from a recombinant yeast *Saccharomyces cerevisiae* strain BJn-5-LA at a scale of 100 liters. Neither of the disclosed methods comprises a precipitation or crystallization step. Further the methods do not require the use of antibodies or monoclonal antibodies specific for factor XIII. Both methods comprise the use of a combination of fractionation methods having different affinity interactions with factor XIII. In a specific embodiment of the present invention, an immobilized metal affinity chromatography (IMAC) step was used and resulted in an improvement in the purity of the rhFXIII. A further objective of the processes was to test a modified down-stream process at the 100 L scale. The protocols comprise several modifications to the down-stream fractionation processes to increase recovery and purity of rhFXIII as compared to prior methods. Butyl-Sepharose™ resin was used as the hydrophopic interaction chromatography (HIC) media in one disclosed process (shown in FIG. 1). This process was also used to produce the rFXIII standard for comparison with another process wherein the butyl derivatized solid phase was replaced by a phenyl-Sepharose™ resin. Use of the phenyl derived HIC media allowed fractionation in a lower salt concentration and provided for broader pooling criteria for the factor XIII enriched fractions. An additional chromatography step was also introduced in the purification process. This additional step comprises fractionation with an immobilized metal affinity chromatography (IMAC) medium, which was carried out after the hydrophobic interaction chromatography (HIC) step. The IMAC resin demonstrated good binding properties for rhFXIII and elution of factor XIII from the resin resulted in the removal of a lower molecular weight contaminant in small-scale experiments. The inclusion of this step in the disclosed process also provided the additional benefit of desalting the sample and significantly reducing the load volume for the final anion exchange step (a Q-Sepharose™ column) from about 600 L down to about 20 L. Overall, the modified process worked successfully at the 100 L scale with a product recovery of about 45%. A schematic of both purification processes is provided in FIGS. 1A through 1C.

Material and Methods

100 Liter Fermenter Production Run:

An inoculum was prepared using recombinant cells that express factor XIII from a working cell bank. The production run was performed in a 100 liter fermenter vessel. A multi-fermenter computer system was used for on-line monitoring of the fermentation process. The oxygen-uptake (OUR), carbon dioxide evolution rate (CER) and respiratory quotient (RQ) were determined. A glucose based yeast culture medium was sterilized by filtration through a 0.2 μm filter. The fermenter was inoculated with a 2nd stage seed tank culture. The glucose feed was filter-sterilized and prepared in batches. Foaming was controlled by manual addition of an antifoam reagent. After the process time the glucose feed was terminated and the pH was increased using an ammonia solution. The culture was then chilled before transferring to down-stream processing.

Down-Stream-Processing of Recombinant Human Factor XIII:

Fermenter harvest was collected and the conductivity was measured. The harvest was conditioned by adjusting to pH 8.5 with 3 M Tris/60 mM EDTA. The conditioned harvest was then homogenized by a single pass through a homogenizer at high pressure. The homogenate, on exit from the homogenizer, was cooled to approximately 15° C. The homogenization process resulted in the production of about 108 L of crude homogenate. The quantity of rhFXIII in the homogenate was measured (activity assay) at 1.6 g/L giving a total of approximately 172.8 g for this particular run.

Expanded Bed Chromatography:

Expanded bed chromatography anion exchange fractionation was performed at ambient temperature using a STREAMLINE 200 Pharmacia column packed with DEAE STREAMLINE resin (Pharmacia). A settled bed height of 42 cm and a column volume (CV) of 13.2 L (i.e., column diameter 20 cm, cross-sectional area 314 cm$^2$) were achieved. Immediately following packing, the column was washed with 4 column volumes (CV) or about 80 L of 10 mM NaOH in down-flow mode and stored overnight.

The homogenate was diluted with two volumes of water resulting in 2 batches of 162 L of 'load' material with a conductivity of 3.9 mS/cm. A conductivity of below 4.4 mS/cm was required for successful capture of rhFXIII on the STREAMLINE resin. The activity assay gave a concentration of 0.6 g/L (100 g total) in batch 1 and 0.5 g/L (81 g total) in batch 2 giving a total of about 181 g rhFXIII. The actual concentration of rhFXIII obtained with a particular run varied and adjustment of the conductivity for each batch was made as required.

The STREAMLINE resin was sanitized using 2 CV of 1 M NaOH at a flow rate of 30 L/h (95.5 cm/hour linear flow rate) in down-flow mode followed by 10 CV purified water at 70 L/h (222.9 cm/hour linear flow rate). The column was then washed with 2 CV of 20 mM Tris/1M Na$_2$SO$_4$, pH 7.8 followed by 8 CV of 20 mM Tris, pH 7.8 in down-flow mode. Conductivity and pH of the flow through buffer were measured to be 2.0 mS/cm and 7.4 respectively. The column was then equilibrated with 20 mM Tris, pH 7.8 in up-flow mode, adjusting the flow-rate to achieve about a 2 fold to about a 2.2 fold bed expansion. The 'load' was pumped through the STREAMLINE column in up-flow mode using a peristaltic pump resulting in a 2.2-fold expansion of the bed (approximately 30 L/h 95.5 cm/hour linear flow rate). Total loading time was approximately 10 h and the pH of the load was checked periodically during loading to ensure that it did not drop below 7.2. Samples of the flow-through were taken every 40 L for later activity assays.

Figure 2:
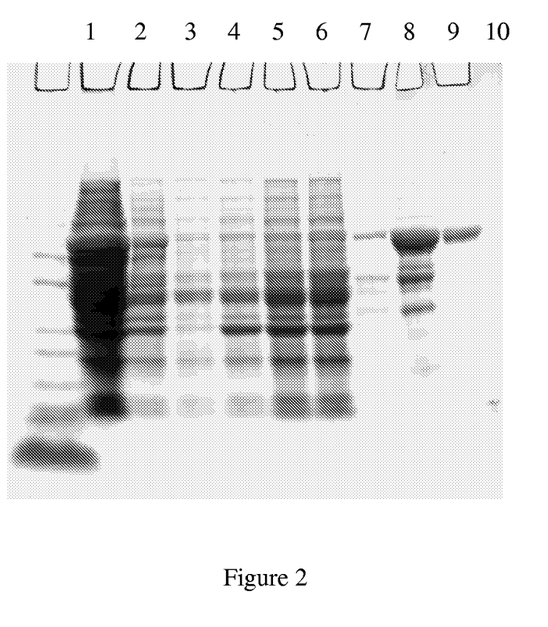
FIG. 2 depicts the results from the SDS-PAGE analysis of fractions collected from the expanded bed DEAE anion exchange chromatography fractionation. Lane 1: molecular weight standards; lane 2: homogenate; Lane 3: load; Lane 4: flow through 40 L; Lane 5: flow through 120 L; Lane 6: flow through 200 L; Lane 7: flow through 280 L; Lane 8: down flow wash; Lane 9: eluate; Lane 10: factor XIII standard.

Loading was followed by 7 CV up-flow wash with 20 mM Tris/25 mM Na$_2$SO$_4$/2% sucrose (w/v), pH 7.8 until the flow-through appeared clear. The flow-rate had to be gradually increased to maintain the 2.2 fold bed expansion. The bed was then allowed to settle and left overnight. The column was washed with 7 CV of 20 mM Tris/25 mM Na$_2$SO$_4$, pH 7.8 in down-flow mode at a flow-rate of 50 L/h (159.24 cm/hour linear flow rate) prior to elution. The elution was carried out using a peristaltic pump by applying 4 CV of elution buffer 20 mM Tris/80 mM Na$_2$SO$_4$, pH 7.8. No detector was used to identify the elution peak and instead all of the elution volume (50 L) was collected. A subsequent activity assay revealed a rhFXIII concentration of 3.2 g/L (159 g total) in the eluate, which corresponds to a recovery of 88% (Table 1). FIG. 2 depicts the SDS-PAGE gel of the expanded bed chromatography fractions. The eluate fraction was stored at 4° C. overnight.

TABLE 1

FXIII Activity Measurements for each Flow though Volume.

| Sample | Activity (g/L) |
| --- | --- |
| Streamline load (324 L) | 0.57 (181 g) |
| Streamline flow though (@ 80 L) | 0.01 |
| Streamline flow though (@ 160 L) | 0.01 |
| Streamline flow though (@ 200 L) | 0.01 |
| Streamline flow though (@ 240 L) | 0.025 |
| Streamline elution (80 mM Na$_2$SO$_4$) | 3.2 g/L (159 g) |

Hydrophobic Interaction Chromatography:

Hydrophobic Interaction Chromatography was carried out at ambient temperature using a Pharmacia BPG 300 column with a packed bed volume of 12 L (i.e., 30 cm column diameter, cross-sectional area 707 cm$^2$) phenyl-Sepharose™ on a Pharmacia 6 mm BioProcess System. The resin was fresh, but was pooled from several lots (Pharmacia). The first factor XIII enriched fraction (the DEAE STREAMLINE eluate) was diluted with an equal volume of 0.5 M Na$_2$SO$_4$ and filtered through a 0.45/0.2 μm filter (Sartobran P). The phenyl-Sepharose™ column was sanitized with 2 CV of 1 M NaOH at 30 L/h (42.43 cm/hour linear flow rate) followed by washing with 5 CV water. The column was then equilibrated with 7 CV of 20 mM Tris/250 mM Na$_2$SO$_4$, pH 7.8. Loading of 100 L conditioned STREAMLINE eluate was carried out at a flow rate of 71 L/h (100.42 cm/hour linear flow rate). Following a wash of 5 CV with 20 mM Tris/250 mM Na$_2$SO$_4$, pH 7.8, the column was eluted with a decreasing sodium sulphate gradient from 20 mM Tris, 200 mM Na$_2$SO$_4$, pH 7.8 to 5 mM Tris, approximately 14 mM $Na_2SO_4$; pH 7.8 over 8.8 CV. The elution peak was collected in 12 fractions of about 9 L, starting collection at UV absorbance >0.1 and stopping collection at UV absorbance <0.1 thus the post-peak material that is eluted with 5 mM Tris alone was avoided. All fractions across the main peak were sampled for analysis prior to being pooled. Samples across the elution were analyzed by SDS-PAGE (see FIG. 3).

Figure 3A:
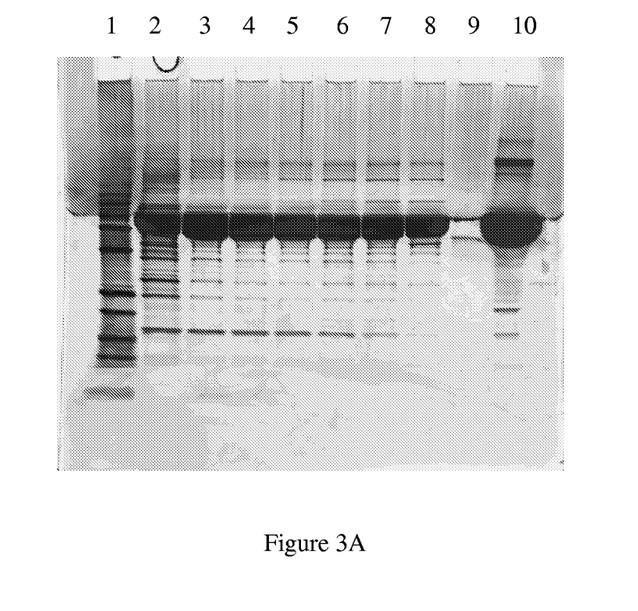
FIGS. 3A and 3B depict the results from the SDS-PAGE analysis of fractions collected from the phenyl-Sepharose™ hydrophobic interaction chromatography step. Lane 1: molecular weight standards; Lane 2: eluate fraction 1; Lane 3: eluate fraction 3; lane 4: eluate fraction 4; Lane 5: eluate fraction 6; Lane 6: eluate fraction 7; Lane 7: eluate fraction 8; Lane 8: eluate fraction 9; Lane 9: eluate fraction 10; Lane 11: molecular weight standards; Lane 12: eluate fraction 11; Lane 13: eluate fraction 12; Lane 14: eluate pool; Lane 15: post peak eluate; Lane 16: load; Lane 17: flow through; Lane 18: wash; Lane 19: bovine serum albumin standard.
Figure 3B:
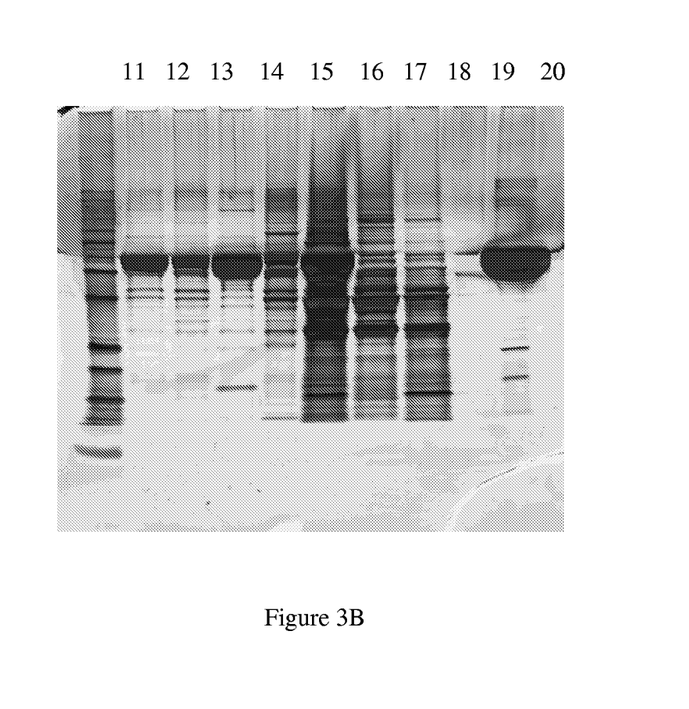

The pooled elution volume (the second factor XIII enriched fraction) was about 105 L, which was measured at 1.3 g/L rhFXIII (137 g total) by activity assay and 1.1 g/L (116 g total) by $A_{280}$. The recovery yield based on the activity assay result was 87% and based on $A_{280}$ measurement was 73%. The pooled eluate was filtered through a 0.45/0.2 µm filter into 'Flexboy' bags and stored at +4° C. for 4 days. FIG. 3 depicts the SDS silver stain gel of the Phenyl Sepharose™ elution samples.

Immobilized Metal Affinity Chromatography (IMAC):

Chromatography was carried out at ambient temperature using a Pharmacia BPG 200 column with a packed bed volume of 4.7 L (i.e., 20 cm column diameter, cross-sectional area, 314 $cm^2$, bed height 15 cm) on a Pharmacia 6 mm BioProcess System. The resin used was chelating Sepharose™ fast flow (Pharmacia). The resin was washed with 5 CV water to remove preservative prior to being charged with 3.5 CV of 250 mM $Ni_2SO_4$, pH 7.8, at 31 L/h (98.7 cm/hour linear flow rate). The column was then equilibrated with 3 CV of 20 mM Tris/0.5 M $Na_2SO_4$, pH 7.8, at 31 L/h to remove any contaminants and excess nickel prior to being equilibrated with 3 CV of 50 mM Tris/100 mM $Na_2SO_4$, pH 7.8, at 31 L/h. The phenyl column eluate pool (105 L) was loaded onto the column at a flow rate of 31 L/h. Column wash was carried out by pumping 1 CV of 50 mM Tris/250 mM $Na_2SO_4$, pH 7.8 at a flow rate of 31 L/h. Factor XIII was eluted using 50 mM Tris, pH 7.8, and the elution peak was collected as soon as the UV trace had risen above baseline. The total elution volume (the third factor XIII enriched fraction) was 8 L, which was immediately diluted to 20 L with 50 mM Tris, pH 7.8, to prevent precipitation, and stored overnight at +4° C.

Figure 4:
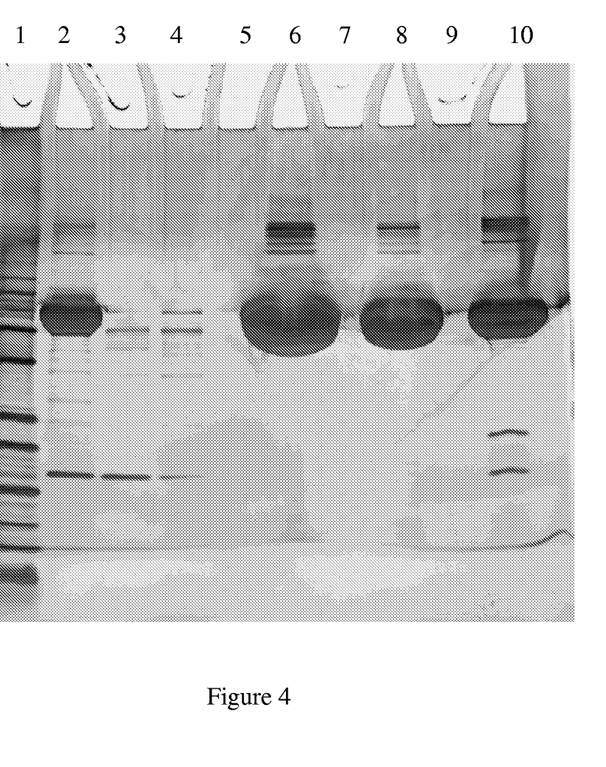

The diluted eluate (volume 20 L) was measured at 5.6 g/L rhFXIII (112 g total) by $A_{280}$. The recovery yield based on the $A_{280}$ result was 96.6%. FIG. 4 depicts the SDS silver stain gel of the IMAC chromatography samples. Samples of IMAC eluate were assayed for residual nickel (RSSL Pharma, Reading UK) and found to have 0.84 ppm Nickel (Table 2).

TABLE 2

Nickel content of samples throughout the process

| Sample | Nickel concentration | | FXIII concentration | | | Molar ratio/ Ni:FXIII |
|---|---|---|---|---|---|---|
| | ppm | µM | ppm | ml | µM | |
| Final Product | <0.02 | <0.34 | 2400 | 2.4 | 28.80 | <0.012 |
| Q-eluate pool | <0.02 | <0.34 | 1000 | 1 | 12.00 | <0.012 |
| IMAC eluate | 0.84 | 14.30 | 5600 | 5.6 | 67.20 | 0.213 |
| Nickel Waste | 1700 | 28.93 mM | N/A | | | |
| Final Product Run 4 | 0.02 | 0.34 | 12000 | 12 | 144.00 | 0.002 |

Anion Exchange Chromatography:

The Q-Sepharose™ resin used in this step had been used previously. It was packed in a Pharmacia BPG 300 column with a packed bed volume of 10.6 L (15 cm column diameter, cross sectional area 707 $cm^2$, bed height 15 cm). The column was sanitized with 2 CV of 1 M NaOH at a flow rate of 30 L/h (42.43 cm/h linear flow rate). The column was then washed with 5 CV of purified water, followed by 3 CV of 100 mM Tris, pH 7.5 and 2 CV of 20 mM Tris/0.5 M $Na_2SO_4$ pH 7.5 to charge the resin with counter ions. The conductivity was then reduced to <3.0 mS/cm by washing the column with 5 CV of 20 mM Tris, pH 7.5. The actual value of the flow through buffer was measured to be 1.46 mS/cm. The diluted IMAC eluate was supplemented with EDTA to a final concentration of 1 mM in order to complex any residual Ni ions present in the IMAC eluate. The load material was then filtered through a 0.45/0.2 µm filter (Sartopore 2) prior to being loaded onto the column. After loading at a flow rate of 71 L/h (100.42 cm/h linear flow rate), the column was washed with 5 CV 20 mM Tris, pH 7.5.

Figure 5A:
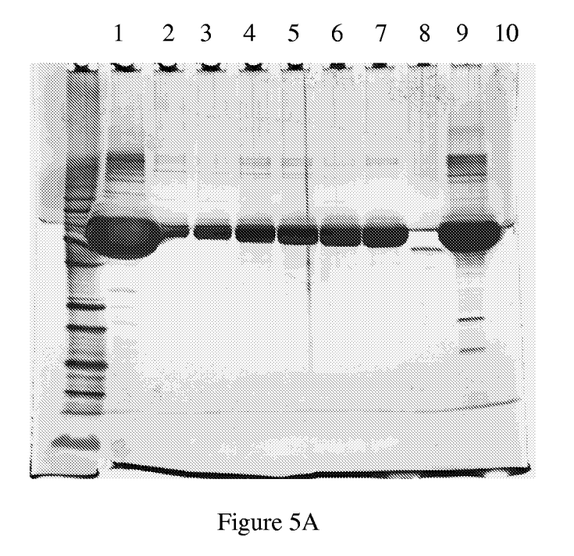
Figure 5B:
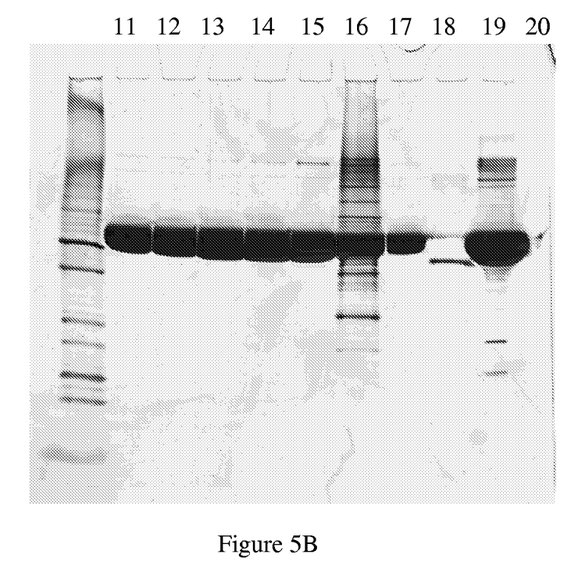

Elution of rhFXIII was carried out by applying a step elution with 20 mM Tris/37.5 mM $Na_2SO_4$, pH 7.5 at a flow rate of 71 L/h. A total of 65 L was collected as pre-peak with the main peak being collected in fractions starting when the UV trace on the BioProcess system reached $OD_{280}$=0.7. A total of 20 fractions (10 fractions of about 9 L, 3 fractions of about 4 L, 7 fractions of about 2 L) were collected and stored over several days at +4° C. while anion-exchange HPLC analysis was carried out on the fractions. From the HPLC analysis all fractions showing 100% purity (fractions 1 through 11 inclusive) were pooled to give a total volume of 90 L. FIG. 5 shows an SDS-PAGE silver stained gel of the load, peak fractions, post peak and eluate pool. The post peak fraction contains significant lower molecular weight bands, which confirms the purification efficacy of this step. The Q-eluate pool (volume 90 L) was measured at 0.88 g/L rhFXIII (79 g total) by $A_{280}$. The recovery yield based on the $A_{280}$ result was 75%. Samples of the Q eluate pool were assayed for residual nickel and found to have <0.02 ppm Nickel. (See Table 2 above).

Ultra-Diafiltration:

In the present example a 30 kDa Molecular Weight CutOff (MWCO) membrane cassette providing a total membrane area of 0.6 $m^2$ was used for diafiltration. Briefly, the eluate from the Q-Sepharose™ chromatography step was diluted with an equal volume of purified water in order to reduce the salt ($Na_2SO_4$) concentration. The diluted eluate pool was then conditioned by adding 25% (w/v) sucrose to a final concentration of 2.5%, giving a total volume of 200 L. The feed was pumped via a peristaltic pump into a 10 L chilled reservoir through a 0.45/0.2 µm filter into a chilled reservoir. Once the reservoir was filled, concentration was started by applying a 3 bar inlet pressure (0 bar outlet pressure) and returning the retentate into the 10 L reservoir.

The material was concentrated from 200 L to 8 L (8.54 g/L by $A_{280}$) and was buffer exchanged with eight volumes of a final formulation buffer containing 20 mM histidine and 4.25% (w/v) sucrose pH 8.0. The diafiltered material (7.2 L) was removed from the apparatus and stored overnight at +4° C.

Figure 6:
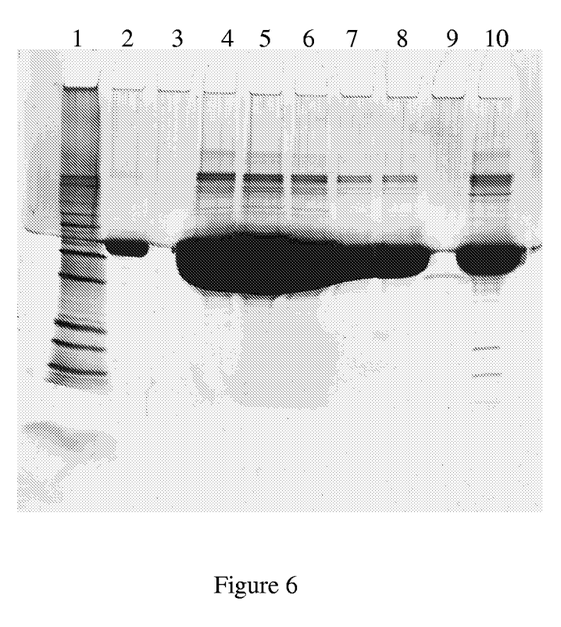

Final Formulation and Analysis:

The diafiltered rhFXIII concentrate fraction was diluted with an equal volume of formulation buffer (20 mM histidine, 4.25% (w/v) sucrose, 0.02% (v/v) polysorbate, pH 8.0). $A_{280}$ measurement resulted in a calculated concentration of 5.4 g/L. The desired concentration was about 2.5 g/L so the material was further diluted with 17.4 L buffer (20 mM histidine, 4.25% (w/v) sucrose, 0.01% (v/v) polysorbate pH 8.0). The final concentration measured by $A_{280}$ was 2.4 g/L. The material was then sterile filtered through a 0.22 Mm filter into a number of aliquots and stored at −20° C. FIG. 6 depicts the result of an SDS-PAGE silver stain analysis of the final product. The concentrated diafiltrate was analyzed for the presence of activated rhFXIII and showed the very low level of 0.19%. The presence of aggregates was measured by SEC-HPLC and demonstrated a very low level of 0.05% (w/w).

The purity of the final product analyzed on Anion Exchange (AIEX) HPLC showed nearly 100% purity, although large molecular weight contaminants were still visible on the silver stain gel. As the gel was overloaded with approximately 70 μg of protein it was not clear whether those bands were artifacts or real contaminants.

The process for purifying rhFXIII has worked successfully at 100 L scale with very good recovery and purity of final product. The use of the phenyl Sepharose™ resin instead of the butyl-Sepharose™ resin had the advantage of operating this step at a lower sodium sulphate concentration and provided a more robust pooling criteria, where the whole peak could be collected when the $A_{280}$ reached 0.1. As expected a better recovery than on the butyl-resin was achieved, i.e., 87% compared to 82% and 74% in the butyl-resin runs. The introduction of IMAC as an additional fractionation step has proven successful, both in terms of recovery of product as well as purification. The results of the PAGE gel (FIG. 4) demonstrated the removal of lower molecular weight bands. Another advantage was the elution of concentrated rhFXIII from this step, which simplified the following process steps immensely since the volume to be loaded onto the anion exchange media (Q-Sepharose™) was reduced from 600 L to 20 L. The Q-Sepharose™ chromatography step was run under the same protocol as all previous 100 L runs and showed good reproducibility. The pooling of elution fractions was based on HPLC results. The protocol can be modified such that the elution peak is collected based on $A_{280}$ of fractions, as all Q-Sepharose™ chromatography runs of the past non-GMP runs have shown the same elution profile. HPLC-analysis of the Q-Sepharose™ elution pool showed close to 100% purity of fhFXIII.

The final ultra-filtration step has been problematic with the flux dropping dramatically when aggregate formation occurred during the course of the filtration. This phenomenon was typically only seen with the larger-scale (100 L) operations, and not with smaller lab-scale purifications. In order to avoid aggregate formation, the material was diluted with an equal volume of water prior to concentration. This did not, however, have an effect on permeate flow rate, which dropped rapidly over time as seen previously. Final product analysis using size-exclusion HPLC demonstrated the presence of an extremely low level of aggregates (0.05% (w/w); Table 3), which indicated that any aggregates that might have been present were not the reason for low permeate flow. The sharp drop in flow does not present a problem for manufacturing scale operations as the surface area of the filtration unit can be increased.

TABLE 3

Final product analysis

| Final Product | FXIII 2.4 mg/ml ($A_{280}$) | Volume 32.4 L | Total FXIII 77.76 g |
|---|---|---|---|
| | FXIII 2.8 mg/ml (activity) | Volume 32.4 L | Total FXIII 90.7 g |
| Activated FXIII | | 0.0121 mg/ml (activity) | 0.019% |
| Aggregates | | | 0.05% |
| Filtered Final Product | FXIII 2.4 mg/ml ($A_{280}$) | Volume 35.6 L | Total FXIII 74.64 g |

Overall, the quality of the final product has been improved and shows much lower levels of aggregates and activated rhFXIII. The process appears to be robust and suitable for scale-up.

The previous examples are provided to illustrate, but not to limit, the scope of the claimed inventions. Other variants of the inventions will be readily apparent to those of ordinary skill in the art and encompassed by the appended claims. All publications, patents, patent applications and other references cited herein are also incorporated by reference herein in their entirety.

What is claimed is:

1. A method for purifying factor XIII from a biological fluid comprising the step of fractionating the biological fluid by immobilized metal affinity chromatography (IMAC), wherein prior to IMAC fractionation, the biological fluid is fractionated by anion exchange fractionation to produce a first fraction enriched for factor XIII and the first fraction enriched for factor XIII is further fractionated by hydrophobic interaction fractionation, and wherein the method does not involve a precipitation step, and wherein the method yields at least about 45% of factor XIII.

2. The method according to claim 1, further comprising a second anion exchange fractionation following the immobilized metal affinity chromatography fractionation.

3. The method according to claim 1, wherein the biological fluid is a cell lysate.

4. The method according to claim 3, wherein the cell lysate is a recombinant yeast cell lysate.

5. The method according to claim 1, wherein the factor XIII is a recombinant factor XIII.

6. The method according to claim 5, wherein the recombinant factor XIII is recombinant human factor XIII.

7. The method according to claim 1, wherein the anion exchange fractionation comprises use of a chromatographic media derivatized with diethylaminoethyl (DEAE) or quaternary aminoethyl (QAE).

8. The method according to claim 1, wherein the hydrophobic interaction fractionation comprises the use of a chromatographic media derivatized with phenyl, butyl, or octyl groups.

9. The method according to claim 8, wherein the chromatographic media is derivatized with phenyl groups.

10. The method according to claim 1, wherein the immobilized metal affinity chromatography fractionation comprises use of a chromatography media charged with $Cu^{2+}$, $Zn^{2+}$, or $Ni^{2+}$.

11. The method according to claim 10, wherein the chromatography media is charged with $Ni^{2+}$.

* * * * *